(12) United States Patent
Tan et al.

(10) Patent No.: US 10,173,002 B2
(45) Date of Patent: Jan. 8, 2019

(54) CATHETER DEVICES WITH NEEDLE GUARDS AND RELATED METHODS

(71) Applicant: B. Braun Melsungen AG, Melsungen (DE)

(72) Inventors: Aik Aun Tan, Penang (MY); Mohd Zairizal bin Zakaria, Penang (MY); E-Jen Teh, Penang (MY); Wen Jenn Lim, Penang (MY); Chee Mun Phang, Penang (MY); Boon Ping Neoh, Penang (MY); Hui Kuun Teoh, Penang (MY); Mohamad Yasin bin Abdulla, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 355 days.

(21) Appl. No.: 14/733,649

(22) Filed: Jun. 8, 2015

(65) Prior Publication Data

US 2016/0354539 A1    Dec. 8, 2016

(51) Int. Cl.
*A61M 5/162* (2006.01)
*A61M 25/06* (2006.01)
(Continued)

(52) U.S. Cl.
CPC .......... *A61M 5/1626* (2013.01); *A61M 5/158* (2013.01); *A61M 5/3273* (2013.01);
(Continued)

(58) Field of Classification Search
CPC .......... A61M 25/0618; A61M 25/0606; A61M 5/3273; A61M 2005/325; A61M 5/158;
(Continued)

(56) References Cited

U.S. PATENT DOCUMENTS

| 5,403,284 A * | 4/1995 | Gross | A61M 25/0606 |
|---|---|---|---|
| | | | 604/167.03 |
| 6,443,929 B1 * | 9/2002 | Kuracina | A61B 5/15003 |
| | | | 604/192 |

(Continued)

FOREIGN PATENT DOCUMENTS

| DE | 202015100911 | 3/2015 |
|---|---|---|
| KR | 20150017771 | 2/2015 |
| WO | WO 2013/014638 | 1/2013 |

OTHER PUBLICATIONS

International Search Report and Written Opinion on corresponding PCT application (PCT/EP2016/062907) from International Searching Authority (EPO) dated Aug. 18, 2016, 11 pages.

(Continued)

*Primary Examiner* — Amber Stiles
(74) *Attorney, Agent, or Firm* — Klein, O'Neill, Singh, LLP

(57) ABSTRACT

Needle devices are described. The needle devices can have a catheter hub, a needle hub, a housing located between the catheter hub and the needle hub. The housing can have an engagement mechanism to removably attach the housing to the catheter hub. The housing can further include a release element to release the engagement mechanism from the catheter hub to disengage the housing from the catheter hub. A flow regulator can be positioned inside the catheter hub. The flow regulator can include a stem and a sleeve.

25 Claims, 13 Drawing Sheets

(51) Int. Cl.
*A61M 25/00* (2006.01)
*A61M 5/158* (2006.01)
*A61M 5/32* (2006.01)

(52) U.S. Cl.
CPC ...... *A61M 5/3275* (2013.01); *A61M 25/0097* (2013.01); *A61M 25/06* (2013.01); *A61M 25/065* (2013.01); *A61M 25/0606* (2013.01); *A61M 25/0631* (2013.01); *A61M 2207/00* (2013.01)

(58) Field of Classification Search
CPC ...... A61M 2005/3247; A61M 25/0631; A61M 25/0612; A61M 5/1626; A61M 39/06; A61M 39/22; A61M 25/06; A61M 5/3275; A61M 25/0097; A61M 25/065; A61M 2207/00
USPC .... 604/110, 164.04, 164.08, 164.09, 167.01, 604/167.03, 192, 246, 256, 263, 264, 272
See application file for complete search history.

(56) References Cited

U.S. PATENT DOCUMENTS

| | | | | |
|---|---|---|---|---|
| 6,616,630 B1* | 9/2003 | Woehr | ............... | A61M 5/3273 604/110 |
| 6,972,002 B2* | 12/2005 | Thorne | ............. | A61M 25/0631 604/164.08 |
| 7,347,839 B2* | 3/2008 | Hiejima | ............ | A61M 39/0606 604/167.04 |
| 7,736,339 B2* | 6/2010 | Woehr | ............... | A61M 25/0618 604/110 |
| 8,496,623 B2* | 7/2013 | Burkholz | .......... | A61M 25/0618 604/164.08 |
| 2003/0199827 A1* | 10/2003 | Thorne | ............. | A61M 25/0631 604/164.08 |
| 2006/0116638 A1* | 6/2006 | Woehr | ............... | A61M 5/3273 604/110 |
| 2007/0093778 A1* | 4/2007 | Cindrich | ............... | A61M 5/158 604/500 |
| 2008/0108944 A1* | 5/2008 | Woehr | ............... | A61B 5/1411 604/164.08 |
| 2008/0312598 A1* | 12/2008 | Douglas | ................ | A61M 5/158 604/167.01 |
| 2009/0131872 A1* | 5/2009 | Popov | ................ | A61B 17/3415 604/164.08 |
| 2012/0184910 A1* | 7/2012 | Woehr | ............. | A61M 25/0606 604/164.08 |
| 2013/0324930 A1* | 12/2013 | Fuchs | ............... | A61M 25/0631 604/164.08 |
| 2014/0276453 A1* | 9/2014 | Woehr | ............. | A61M 25/0618 604/246 |
| 2015/0151085 A1* | 6/2015 | Tan | ................... | A61M 25/0618 604/164.08 |
| 2016/0106959 A1* | 4/2016 | Woehr | ............. | A61M 25/0097 604/125 |
| 2017/0251966 A1* | 9/2017 | Crawford | ............. | A61B 5/1422 |

OTHER PUBLICATIONS

International Preliminary Report on Patentability (Chapter I) on corresponding PCT application (PCT/EP2016/062907) from International Searching Authority (EPO) dated Dec. 21, 2017, 8 pages.

* cited by examiner

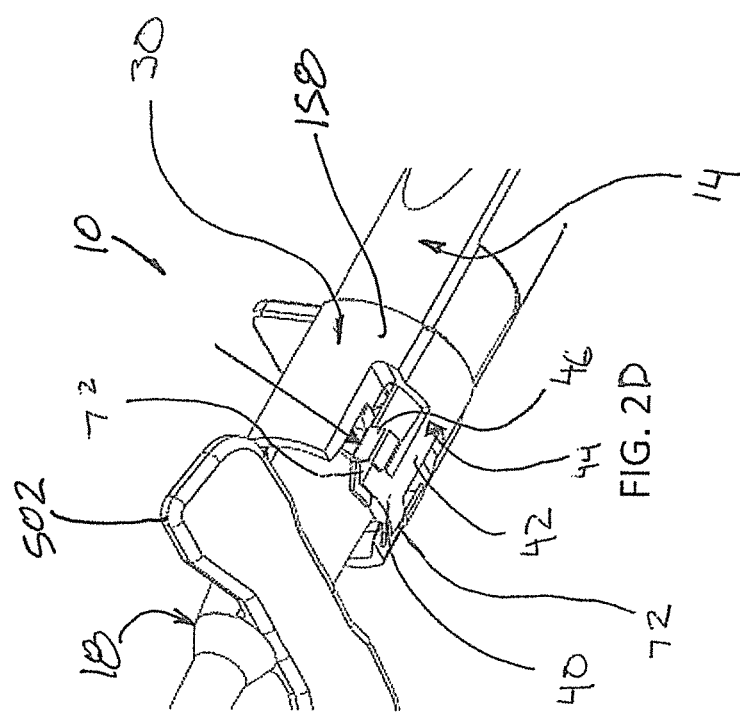

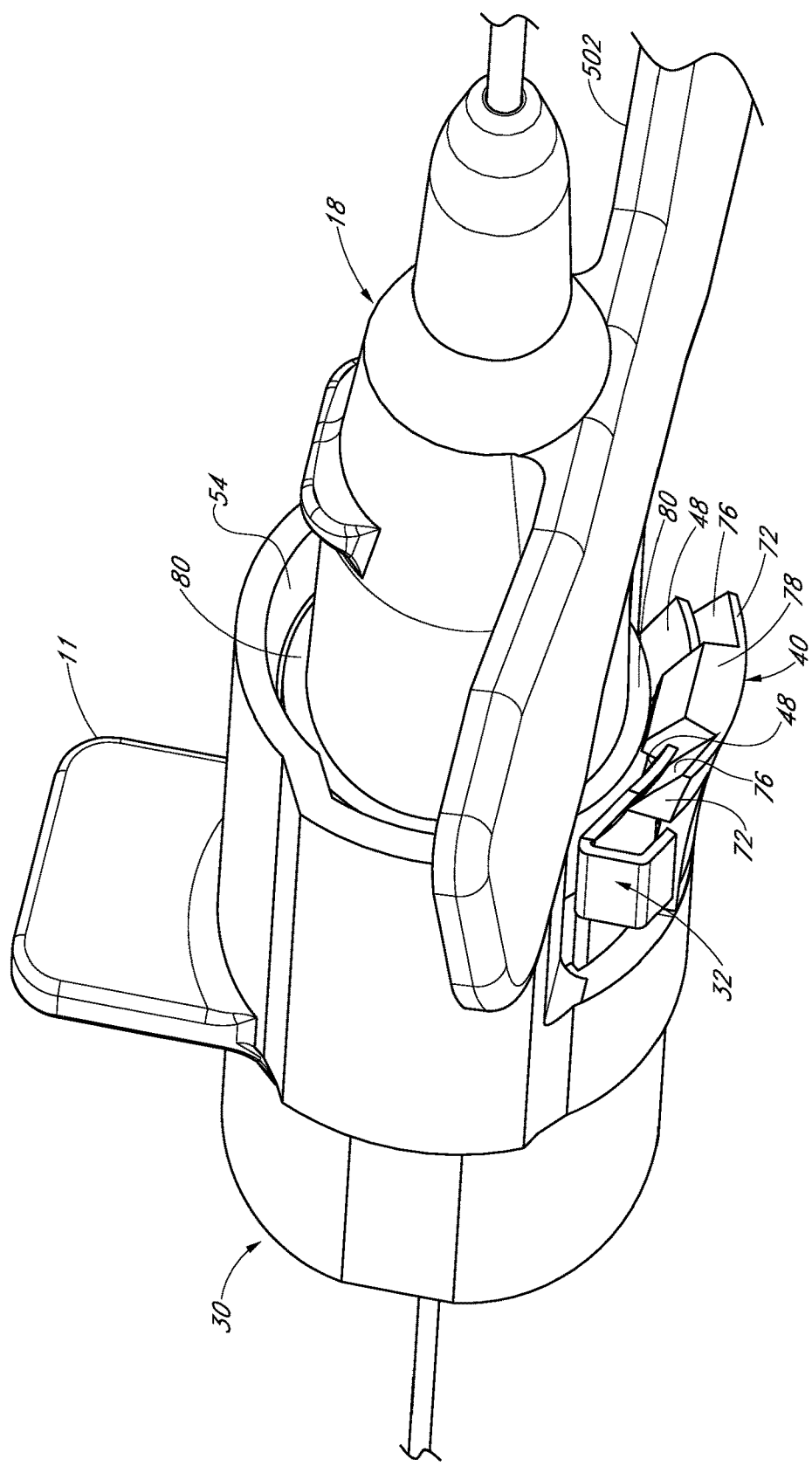

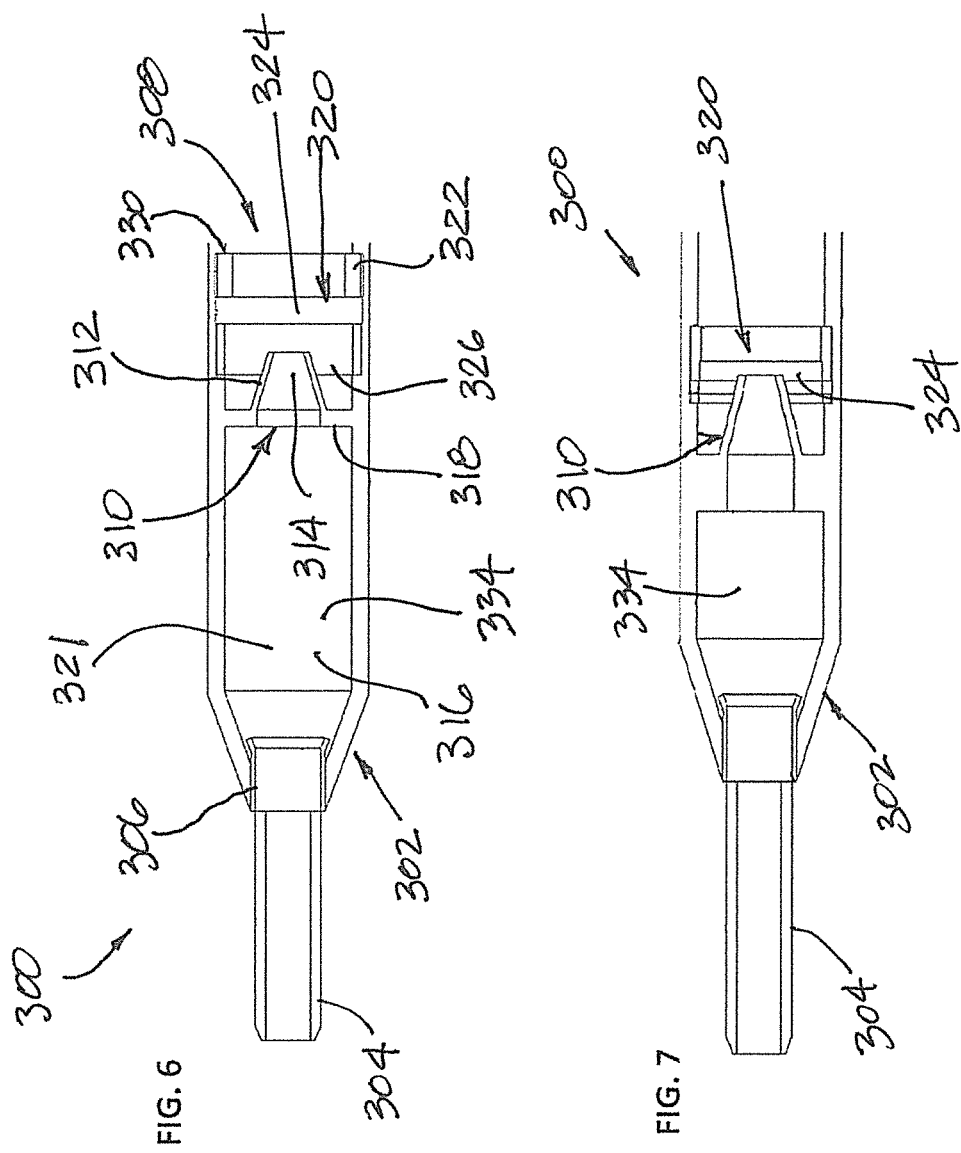

CATHETER DEVICES WITH NEEDLE GUARDS AND RELATED METHODS

FIELD OF ART

The disclosed invention generally relates to intravenous (IV) infusion devices or apparatuses, including IV and arterial catheters. In particular, catheter devices having a flow control system and a needle guard system are disclosed.

BACKGROUND

Needle devices are commonly used for a variety of infusion therapies, including infusing fluids into a patient, withdrawing blood from a patient, or monitoring various parameters of the patient's vascular system. A catheter tube connected to a catheter hub is typically connected to an adapter then connects to an IV tubing. Blood control catheters include an internal blood control regulator, such as a valve, that is opened by the insertion of a male Luer or other object into a proximal end of the catheter hub. Thus, following placement of the catheter tube into the vasculature of a patient, an IV fluid source can be connected to the catheter hub, opening the blood control valve. Once connected, fluid from the IV source can begin flow into a patient through the catheter. Conventionally speaking, the proximal end is the end closer to the practitioner and the distal end is further away from the practitioner, relative to the proximal end.

Needle devices often include safety systems that cover the tip of the needle to prevent accidental sticks after placement of the catheter tube into the vasculature of a patient. These systems can be either passive or active. In some systems, the safety features are located inside the catheter hub in the ready position while in other systems they are external of the catheter hub. In either location, the safety features serve the same function, to cover the needle tip in order to prevent accidental needle sticks after venipuncture.

SUMMARY

Aspects of the present disclosure include a needle device comprising: a needle hub; a needle extending from a distal end of the needle hub; a catheter hub distal of the needle hub and comprising, an interior cavity, a first section and a second section, the first section being distal of the second section; a housing located at least in part in between the catheter hub and the needle hub and having a movable arm; a release element located at least partially inside the housing and in mechanical communication with the movable arm; and wherein part of the arm on the housing engages an exterior of the catheter hub and wherein the arm is deflectable by action of the release element which is deflectable by action of the needle to release the engagement between the part of the arm and the exterior of the catheter hub.

An aspect of the present disclosure is understood to include a needle device comprising a catheter hub with a catheter tube, a flow control regulator positioned inside the interior cavity of the catheter hub, a needle guard positioned inside a shroud of a housing, which is removably engaged to the catheter hub, and a needle hub having a needle projecting through the housing, the needle guard, the catheter hub, and the catheter tube and having a tip extending distally out a distal opening of the catheter tube. The needle hub can optionally include a distal receiving space for receiving a proximal elongated section of the housing. The needle hub can optionally include distally extending wall panels that straddle two sides of the housing. The flow control regulator can comprise a compressible elastic sleeve. The flow control regulator can comprise an elongated stem with a flow channel located inside the compressible elastic sleeve.

A release element may be positioned inside the housing and has a proximal wall that is located between a proximal wall of the needle guard and a proximal wall of the housing. The release element can include lifters for interacting with an arm on the housing. The housing can engage the catheter hub by way of a projection on the arm. The projection can separate from a notch on the catheter hub by causing the lifters on the release element to push the arm of the housing radially outwardly away from a lengthwise axis of the device. The pushing action by the lifters can resemble a camming action between tapered surfaces on the lifters and tapered surfaces on a flared end of the arm. The needle can comprise a change in profile. The change in profile can engage a perimeter defining an opening on the needle guard when the needle moves in a proximal direction following successful venipuncture. Upon retraction of the needle guard by the needle, the needle guard can push on the release element, which can cause the lifters to move the arm to separate from the catheter hub. Further retraction of the needle can separate the housing from the catheter hub.

Another aspect of the present disclosure includes a needle device comprising a needle hub with a needle, a catheter hub with a catheter tube, a guard housing removably secured to the catheter hub, and wherein the needle projects through the guard housing, the catheter hub, and the catheter tube.

The needle device, wherein the guard housing can include a release element and a latch removably attached to the catheter hub.

Still yet other aspects of the present disclosure include a needle device comprising: a needle hub with a needle with a needle tip extending in a distal direction; a catheter hub distal of the needle hub and comprising an interior cavity and a catheter tube extending distally of a distal end of the catheter hub; a guard housing located at least in part between the catheter hub and the needle hub and having a movable arm; a release element located at least partially inside the guard housing and in mechanical communication with the movable arm; wherein the needle projects through the guard housing, the catheter hub, and the catheter tube and out a distal end of the catheter tube in a ready to use position; and wherein part of the arm on the guard housing engages an exterior of the catheter hub and the arm is deflectable by action of the release element, which is movable by action of the needle to release the engagement between the part of the arm and the exterior of the catheter hub.

The device wherein the arm can be movable by a camming motion.

The device can further comprise a needle guard comprising a proximal wall having a perimeter defining a proximal opening located in the guard housing.

The device wherein the needle guard can contact the release element.

The device can further comprise a flow regulator located in the interior cavity of the catheter hub.

The device wherein the arm can comprise a latch with a projection that engages the catheter hub.

The device wherein the latch can include both a projection and at least one sloped operative surface.

The device wherein the projection can engage a ridge formed on an exterior of the catheter hub.

The device wherein the ridge can be formed by an annular recess or a recess section on the exterior of the catheter hub.

The device wherein the flow regulator can comprise an elongated stem and a compressible sleeve surrounding the elongated stem.

The device wherein the release element can comprise at least one lifter.

The device wherein the release element can include a proximal wall with a perimeter defining an opening, a short leg, and a long leg, which is longer in length than the short leg.

The device wherein the short leg can include a distal edge blocked by a shoulder in the interior cavity of the catheter hub from moving in a distal direction.

The device wherein the short leg can include a bend to define a first sloped section and a second section.

The device wherein the long leg can comprise two lifters and wherein the two lifters are tapered relative to a lengthwise axis of the needle.

The device wherein the two lifters can be in contact with two sloped operative surfaces on the arm.

The device wherein a camming motion can be generated when the two lifters are moved relative to the two sloped operative surfaces.

The device can further comprise a projection located between two sloped operative surfaces.

The device can further comprise two retainers defining a space for receiving at least part of the arm on the guard housing.

The device wherein the needle can incorporate a change in profile for engaging the needle guard.

The device wherein the guard housing can include a proximal elongated extension projecting into the needle hub.

The device wherein the needle hub can include two spaced apart wall panels for receiving the proximal elongated extension.

The device the elongated stem can comprise a base fitted against an interior surface of the catheter hub.

The device wherein the elongated stem can include a blunt end and a flow path.

The device wherein the elongated stem can comprise a conical projection having a flow path.

The device wherein the elongated stem can attach to a flange.

The device wherein the compressible sleeve can comprise a septum.

The device wherein the needle guard can comprise two arms that intersect one another along a side view in both the ready to use position and in a protective position.

The device wherein the compressible sleeve can include a proximal end surface that is flushed with a proximal end of the catheter hub.

The device wherein the elongated stem can be configured to push through a septum, on the compressible sleeve.

The device wherein the elongated stem can be configured with a dimension that fits inside a tip of a male medical implement.

The device can further comprise pair of wings extending from the catheter hub.

The device wherein the arm can be unitarily formed with the guard housing.

The device wherein the guard housing can include a proximal wall with a perimeter defining an opening having the needle passing therethrough.

The device wherein the release element can include a proximal wall having a perimeter defining an opening having the needle passing therethrough.

The device wherein the proximal wall of the release element can be spaced from the proximal wall of the guard housing a first distance when in the ready to use position and by a second distance when in an activated position, and wherein the second distance is less than the first distance.

The device wherein the second distance can be less than 5 mm, such as 4 mm, 3 mm, or 2 mm. The second distance can also be zero.

The device wherein the projection can engage exterior threads formed on an exterior of the catheter hub.

The device can further comprise a plug attached to a proximal end of the needle hub.

The device wherein the compressible sleeve can comprise a plurality of folds when compressed by a male medical implement.

The device wherein the arm can be located externally of the long leg.

The device wherein retainers can extend from the long leg and wrap, at least in part, around the arm.

Other aspects of the present disclosure include a method of manufacturing a needle device. The method can comprise: forming a needle hub with a needle with a needle tip extending in a distal direction; forming a catheter hub comprising an interior cavity and a catheter tube extending distally of a distal end of the catheter hub and placing the catheter hub distal of the needle hub; forming a guard housing with a movable arm and placing the guard housing at least in part between the catheter hub and the needle hub; placing a release element at least partially inside the guard housing and in mechanical communication with the movable arm; wherein the needle projects through the guard housing, the catheter hub, and the catheter tube and out a distal end of the catheter tube in a ready to use position; and wherein part of the arm on the guard housing engages an exterior of the catheter hub and the arm is deflectable by action of the release element, which is movable by action of the needle to release the engagement between the part of the arm and the exterior of the catheter hub.

BRIEF DESCRIPTION OF THE DRAWINGS

These and other features and advantages of the present devices, systems, and methods will become appreciated as the same becomes better understood with reference to the specification, claims and appended drawings wherein:

FIG. 2D shows a bottom perspective view of the catheter hub and needle hub with the housing and the release element of FIG. 2C disposed, at least in part, between the catheter hub and the needle hub;

FIG. 3D shows a partial perspective of needle device of FIG. 3C from a different viewing angle;

FIG. 6 shows a schematic side cross section view of an alternative needle device in a ready to use position; and FIG. 7 shows the needle device of FIG. 6 in a valve opened position.

DETAILED DESCRIPTION

The detailed description set forth below in connection with the appended drawings is intended as a description of the presently preferred embodiments of catheter devices or assemblies provided in accordance with aspects of the present apparatuses and methods and is not intended to represent the only forms in which the present apparatuses and methods may be constructed or utilized. The description sets forth the features and the steps for constructing and using the embodiments of the present apparatuses and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1A:
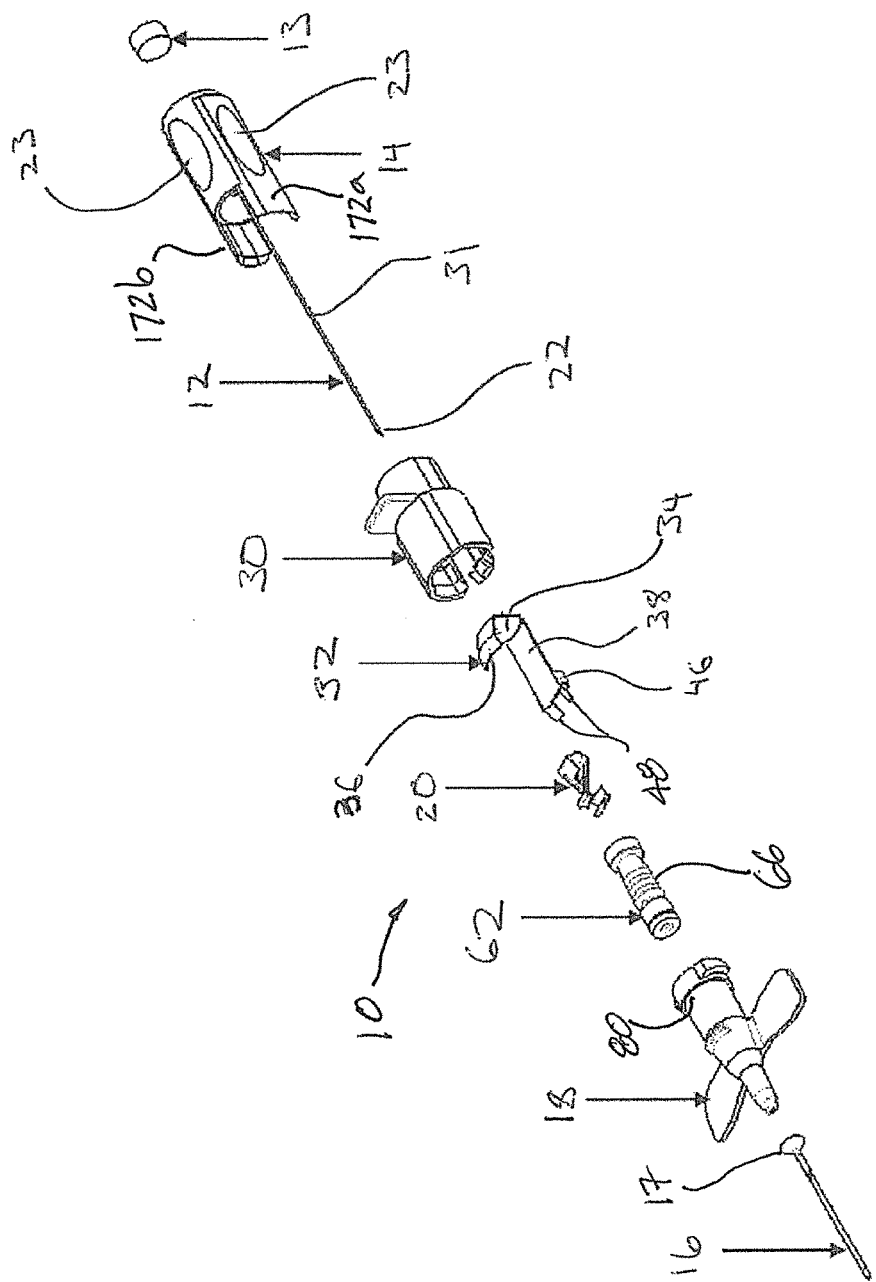
FIG. 1A shows an exploded perspective view of a needle device or assembly in accordance with aspects of the disclosure.

FIG. 1A is an exploded perspective view of a needle device 10, also interchangeably referred to as a needle assembly or catheter assembly, provided in accordance with aspects of the present disclosure. The needle device 10 comprises a needle 12 attached to a needle hub 14, a catheter tube 16 and a ferrule 17 for retaining the catheter tube 16 to a catheter hub 18, a guard housing 30 (or simply housing 30), a plug 13, such as a vent plug, and a needle guard 20. Also shown are a flow regulator 62, which includes a compressible piston, compressible sleeve, or sleeve element 66, and a release element 32. The needle guard 20 is sized and shaped to cover the tip 22 of the needle 12 after the needle is withdrawn following successful venipuncture. The needle device 10 may also be referred to as a safety catheter assembly or a safety catheter device.

Grip panels 23 are formed on the needle hub 14 to assist a user to grip the needle hub during withdrawal of the needle 12 away from the catheter tube 16 following successful venipuncture. The needle device 10 disclosed in FIG. 1A has a generally circular cross section and a lengthwise axis. However, other cross sectional shapes are contemplated. For example, the needle device may have a generally square, triangle, hexagonal, octagonal, or diamond shaped cross section. When the needle device 10 is assembled in a ready to use position, similar to that shown in FIG. 2A, the needle tip 22 projects out a distal end of the catheter tube 16 for placement of the catheter tube into a vein. The needle hub 14 is located immediately proximal of the guard housing 30 and the needle guard 20 is positioned outside and proximal of the catheter hub 18 and distal of the needle hub 14.

The release element 32 shown in FIG. 1A is configured to be activated to release the guard housing 30 from the catheter hub 18. When assembled, the needle guard 20 is located with the release element 32 and the combination release element 32 and needle guard 20, which may be referred to as a guard trigger 35, is located within the holding space of the guard housing 30. As further discussed below, upon activation of the guard trigger 35, the needle guard 20 covers the needle tip 22 of the needle 12 while the release element 32 releases the engagement between the guard housing 30 and the catheter hub 18 to permit separation of the guard housing from the catheter hub. The guard housing 30 with the release trigger 35 is shown in FIG. 2B. The guard housing 30 may be assembled as shown prior to engagement with a catheter hub.

With reference now to FIG. 2B in addition to FIG. 1A, the exemplary needle guard 20 can comprise a proximal wall 24 having a perimeter 140 defining an opening, also referred to as a proximal opening, two arms 26 extending distally of the proximal wall 24, and a distal wall 28 located on each arm for blocking the needle tip 22. Each distal wall 28 can have a curved lip as shown by rolling the end into a hook or can terminate with a straight edge, which is less preferred. The two arms 26 can intersect one another when viewed from a side in both a ready to use position and in a protective position in which the distal walls are located in front of the needle tip. Further information regarding the needle guard 20 is disclosed in U.S. Pat. No. 8,647,313. The needle 12 is shown projecting through the guard housing 30, the release element 32, and the needle guard 20. The needle 12 has a needle shaft 31, a tip 22, and optionally a change in profile 29 when used with a needle guard 20. The change in profile 29 can comprise a crimp, a bulge, a sleeve, or a material buildup, near the needle tip 22 for interacting with the needle guard 20, such as to engage the perimeter 140 defining the opening on the proximal wall 24, during retraction of the needle 12 in a proximal direction following placement of the catheter tube into a patient's vein. Conventionally speaking, proximal direction or proximal end generally designates the end closer to the practitioner and distal, distal direction or distal end generally designates the end opposite the proximal end.

With continued reference to FIG. 2B and FIG. 1A, the needle shaft 31 is connected at or near its proximal end to the needle hub 14 by conventional means. The distal end of the needle hub 14 comprises an opening and two spaced apart wall extensions or wall panels 172a, 172b for receiving the housing 30 in a ready to use position. Following successful venipuncture, the needle hub 14 is separated from the catheter hub 18, withdrawing the needle 12 from the catheter tube 16 and the catheter hub 18, and causing the change in profile 29 on the needle shaft 31 to engage the needle guard 20. As further discussed below, this proximal needle movement causes the needle guard 20 to move the release element 32 to then activate a latch 40 to separate the guard housing 30 from the catheter hub 18. The catheter tube 16 remains in the punctured vasculature (not shown). In some examples, the needle guard is omitted from the needle device 10. For example, the release element 32 can be provided with a distal wall or a trap to cover the needle tip without separately using a needle guard.

Figure 1B:
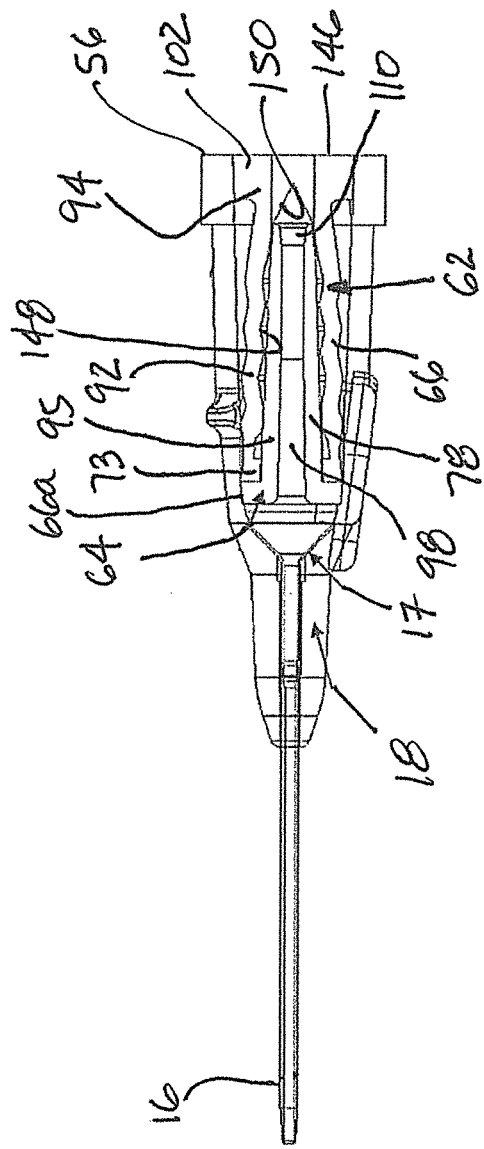
FIG. 1B shows a side cross section of the catheter hub of FIG. 1A with a flow regulator in a closed position.
Figure 1C:
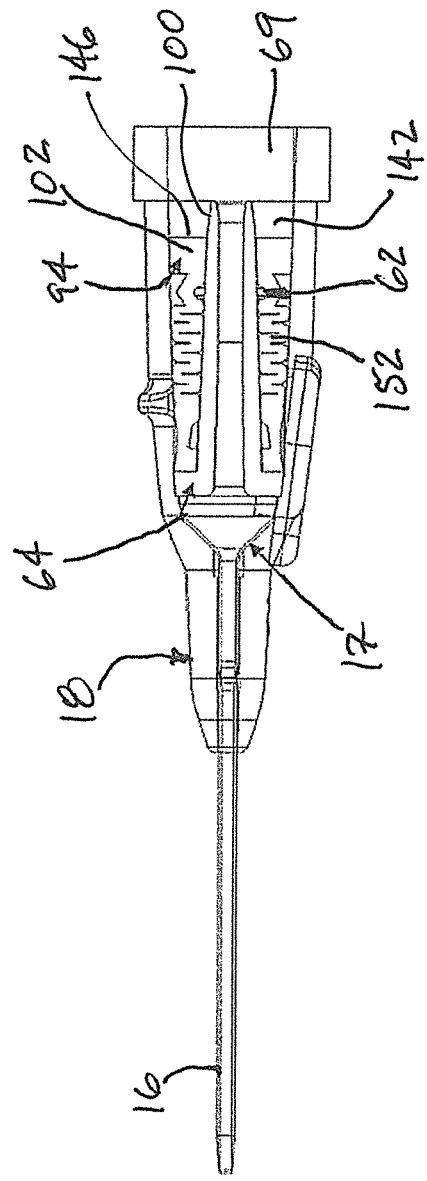
FIG. 1C shows a side cross section of the catheter hub with the flow regulator of FIG. 1B in the activated or opened position, such as when pressed by a tip of a male medical implement.

The needle device 10 of the present embodiment can also include a flow regulator 62, which can embody and pliable and compressible piston or sleeve element 66, as shown in FIG. 1A, and an actuator 95, such as an elongated stem 78 (FIGS. 1B and 1C). The sleeve element 66 of the flow regulator 62 is configured to be used with the stem 78 comprising a lumen or flow path 98, which is more clearly shown in FIGS. 1B and 1C. In some examples, the sleeve element 66 regulates fluid flow through the catheter hub without an actuator 95. The sleeve element 66 can be located in an interior cavity or bore 142 of the catheter hub 18 and be sized and shaped to surround the elongated stem 78 of the actuator 95 so that its proximal end surface 146 is generally even with a proximal end 56 of the catheter hub 18. This even or flushed configuration allows the proximal end surface 146 of the sleeve element 66 to be cleaned, such as to be wiped with an antiseptic cleaner. In other examples, the proximal end surface 146 of the flow regulator 62, such as the proximal end 146 of the sleeve element 66, can be shorter and can be recessed from the proximal end 56 of the catheter hub 18. In still other examples, the flow regulator is omitted. In yet other examples, a different valve and a different valve opener are used.

In the embodiment shown, the actuator 95 is made from a rigid structure or a semi-rigid structure and located inside the sleeve element 66, which may be made from an elastomeric material such as silicone. In an example, the actuator 95 is made from a rigid or semi-rigid plastic and placed or positioned within the bore or interior cavity 142 of the catheter hub 18. The actuator 95 comprises a base 64 attached to the elongated stem 78. The elongated stem 78 defines a hollow interior 98, which defines a fluid flow path or lumen. The fluid flow path 98 is in fluid communication with the interior of the catheter hub, near the base 64, the lumen of the catheter tube 16, and a male medical implement used to open the sleeve element 66, as further discussed below.

The base 64 of the actuator 95 comprises a generally flattened disc having a circumferential edge 66a. As shown, the base 64 contacts an interior of the distal wall of the catheter hub 18 and the circumferential edge 66a contacts the interior surface of the bore 142. The elongated stem 78 extends in a proximal direction from the base 64 and terminates in a blunt tip 100, which has an opening at a central proximal most end. In another example, the blunt tip has a closed proximal most end with one or more side openings near the tip 100 for fluid flow. In some examples, the elongated stem 78 has a tip 100 with a sharp end, instead of a blunt end, with one or more flow openings on the side of the sharp tip 100. The pointed end or the blunt end of the elongated stem 78 is configured project through the proximal sealing element 102 of the sleeve element 66, as further discussed below. The flow regulator 62 may be installed inside the catheter hub 18 by pushing the sleeve element 66 and the elongated stem 78 into the bore 142 until the base 64 contacts a shoulder inside the bore 142, at which time the distal end 73 of the sleeve element 66, which can embody a flange, is wedged inside the bore 142 between the elongated stem 78 and the interior surface of the bore 142. A separate locking ring or other mechanical engagements are contemplated for securing the sleeve element 66 inside the bore 142. For example, a washer may be used to wedge the distal end 73 of the sleeve element 66 against the base 64 of the elongated stem 78.

The sleeve element 66 comprises a compressible body 92 having proximal sealing element 102 with a septum 94, which can have one more slits to be opened by the tip 100 of the elongated stem 78 when the sealing element 102 is pushed in the distal direction into the tip 100 of the stem 78 by a male medical implement inserted into the proximal opening 69 of the catheter hub 18, such as a by male Luer tip for mated fitting with a female Luer of the catheter hub 18. The proximal sealing element 102 of the sleeve element 66 has a side surface that contacts the interior surface of the catheter hub 18 and a proximal end surface 146 that is generally flushed with the proximal end 56 of the catheter hub 18. The flushed arrangement presents a face at the proximal opening of the catheter hub for wiping or cleaning the proximal sealing element 102, such as with an antiseptic swab. When the flow regulator 62 is in a closed position shown in FIG. 1B, the interior wall surface of the bore 142 of the catheter hub 18 confines the proximal sealing element 102 so that the one or more slits of the septum 94 are pressed closed by the constraint of the catheter hub. In the example shown, the sleeve element 66 has an interior wall surface defining a bore 148 having the elongated stem 78 positioned therein. The sleeve element 66 is selectively compressible to expose the tip 100 of the elongated stem 78 by a male medical implement, such as a syringe tip, so that fluid communication is enabled between the male medical implement and the catheter tube 16.

When a male medical implement is inserted into the open proximal end 69 of the catheter hub 18, the male medical implement contacts the proximal end surface 146 of the proximal sealing element 102 and moves it distally. This causes the compressible body 92 to compress around the elongated stem 78 of the rigid actuator 95. As shown, a conical shaped recess 150 (FIG. 1B) is provided on the interior wall surface of the proximal sealing element 102 to facilitate opening the one or more slits by the tip 100 of the elongated stem 78. For example, when the proximal sealing element 102 is pushed in a distal direction by a syringe tip, the conical shaped recess 150 is pushed against the tip 100 of the elongated stem 78, which then spreads open the one or more slits of the septum 94 to open the flow regulator 62 for fluid flow through the catheter hub 18. In one example, the compressible body 92 is compressed into random folds 152 when opened by a male medical implement. In other examples, notches or weakened sections can be provided with the wall surfaces of the compressible body 92 so that when the sleeve element 66 is compressed, the folds form pre-determined fold sections, such as ring sections. Once the one or more slits of the septum 94 is opened, the catheter tube 16 is in fluid communication with the male medical implement through the hollow interior 98 of the elongated stem 78. As shown in FIG. 1C, the flow regulator 62 is configured so that the proximal end surface 146 of the proximal sealing element 102 is pressed distal of the tip 100 of the elongated stem 78 when opened by a male medical implement. This arrangement ensures that the tip 100 of the elongated stem 78 enters into the bore of the male medical implement when the flow regulator 62 is opened. In another example, the tip 100 is arranged to abut a distal end edge of the male medical implement so that the proximal end surface 146 of the proximal sealing element 102 is pressed approximately even with the tip 100 of the elongated stem 78 when opened by the male medical implement.

Figure 2A:
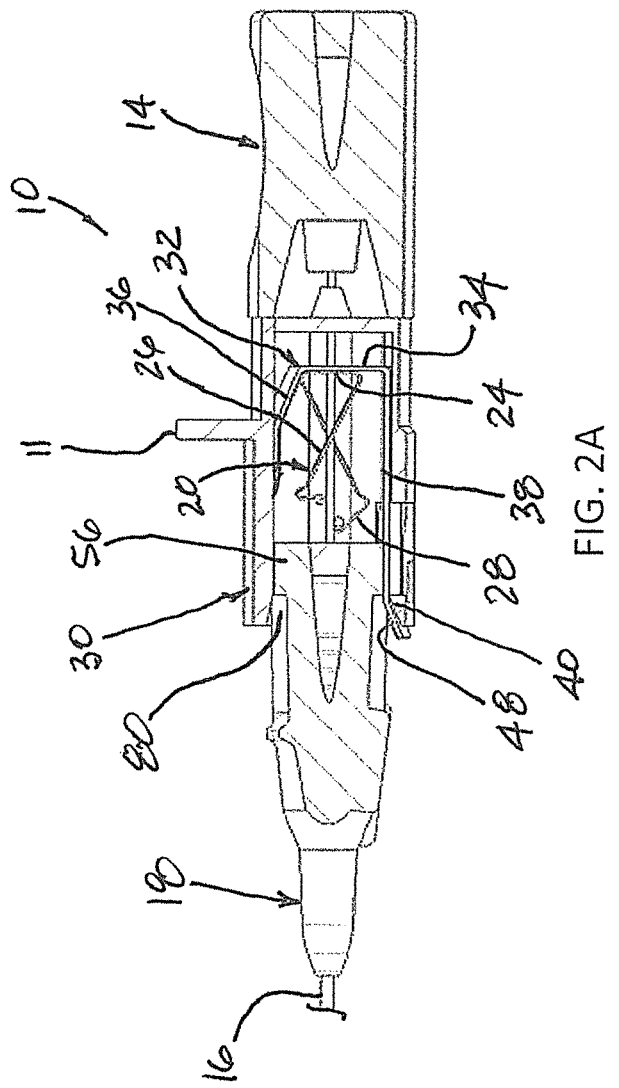
FIG. 2A shows a side cross sectional view of the needle device of FIG. 1A in an assembled and ready to use position, with a needle guard.
Figure 2B:
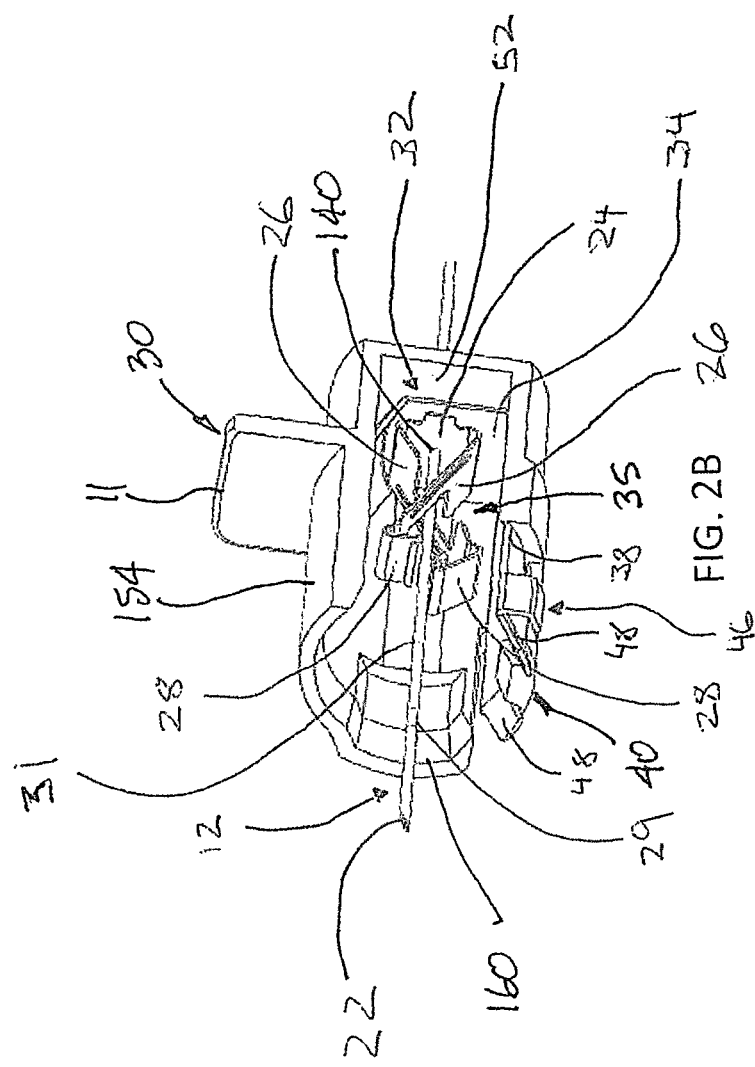
FIG. 2B shows a cut away perspective cross sectional view of a guard housing of FIG. 2A with a needle guard and a release element.
Figure 2C:
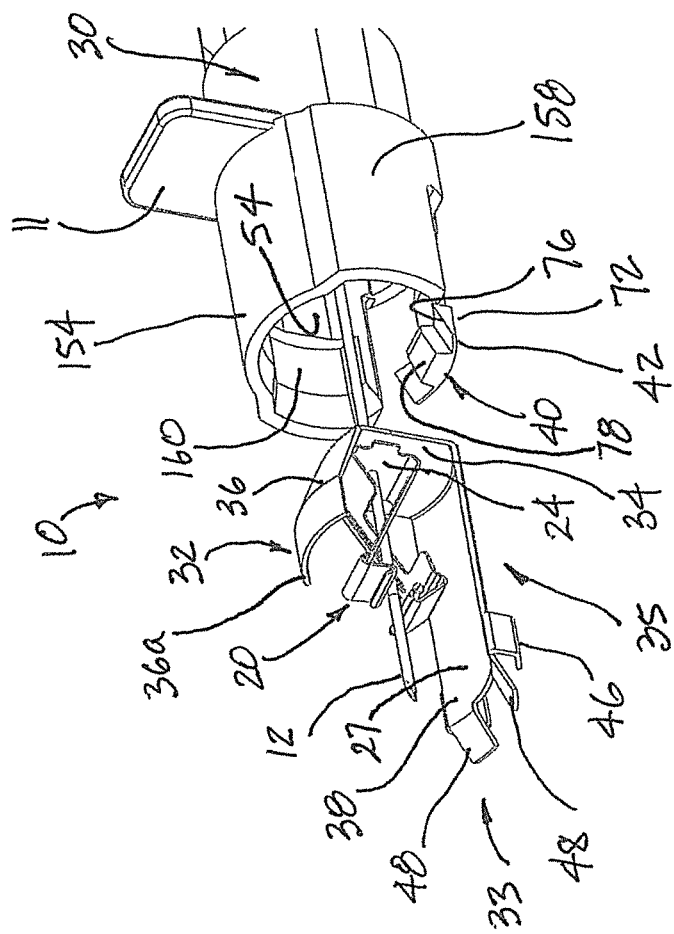
FIG. 2C shows a needle guard next to a release element prior to placement of the needle guard and the release element into the guard housing to then secure or attach to a catheter hub.

With reference now to FIG. 2C in addition to FIG. 1A and FIG. 2B, the needle device 10 includes a release element 32 to facilitate the release of the guard housing 30 from the catheter hub 18, such as to release a latch from the catheter hub. As shown, the release element 32 comprises a proximal wall 34, a short leg 36, and a long leg 38. In an example, the short leg 36 includes a continuous length with or without one or more kinked sections or bends. When incorporated, the one or more bends form distinct sections on the short leg 36. The short leg 36 may have a uniform width or different widths along the length thereof, such as a variable width. The long leg 38 can also have a variable width or a single width along a length thereof. In the example shown, the short leg 36 of FIG. 2C has a bend so that the short leg 36 has a sloped proximal section and a generally horizontal distal section 36a. In other examples, the short leg does not include any bend. The distal section 36a of the short leg has an arc surface to form a close fit with the interior of the guard housing 30. The long leg 38 has a distal end 33 that includes two retainers 46 extending from the two side edges of the long leg and each with a free end that points in the direction of the lengthwise axis of the long leg 46. The long leg 38 further comprises two lifters 48 that point in a distal direction from a distal end of the long leg 38. In other examples, only one lifter or more than two lifters are incorporate. Also, one or more than two retainers can be used with the release element. The two lifters 48 are spaced from one another by a gap and each are tapered relative to the generally horizontal surface of the body 27 of the long leg 38. The two lifters 48 are spaced from one another and resemble two tines extending from a distal end of the long leg 38. In an example, the lifters 48 and the retainers 46 resemble tabs that are folded from the body 27 of the long leg. The release element 32 may be made by stamping a metal sheet and then folding the various sections into the shape shown, which includes a short leg 36, a proximal wall 34, a long leg 38, lifters 48, and retainers 46. The two retainers 46 are spaced from one another and define a space therebetween for receiving an extension or arm 42 (FIG. 2C) on the housing 30 and/or the terminal end 40 of the arm 42, which is attached to the wall surface 158 of the guard housing 30 at its base 44. The terminal end 40 is configured to engage the catheter hub 18 and may be understood to be a latch. The latch 40 can comprise a projection 78 located between two ramps 72, each with a sloped operative surface 76.

With further reference to FIG. 2C, the housing 30 has a shroud 154 and a push flange or tab 11 extending from the shroud in 154 a radially outward direction relative to the lengthwise axis of the device 10. The tab 11 may be used as leverage during placement of the catheter tube and/or during retraction of the needle following placement of the catheter tube. The shroud 154 has a wall surface 158 defining an interior receiving space 160 for receiving the release element 32 and the needle guard 20. The arm 42 and the terminal end or latch 40 are shown with the guard housing 30. When mounting the guard trigger 35 inside the receiving space 160 of the guard housing 30, the terminal end 40 of the arm 42 slides between the two retainers 46 of the release element 32 and rest next to or in abutting contact with the two lifters 48 on the long leg 38 of the release element.

Figure 4:
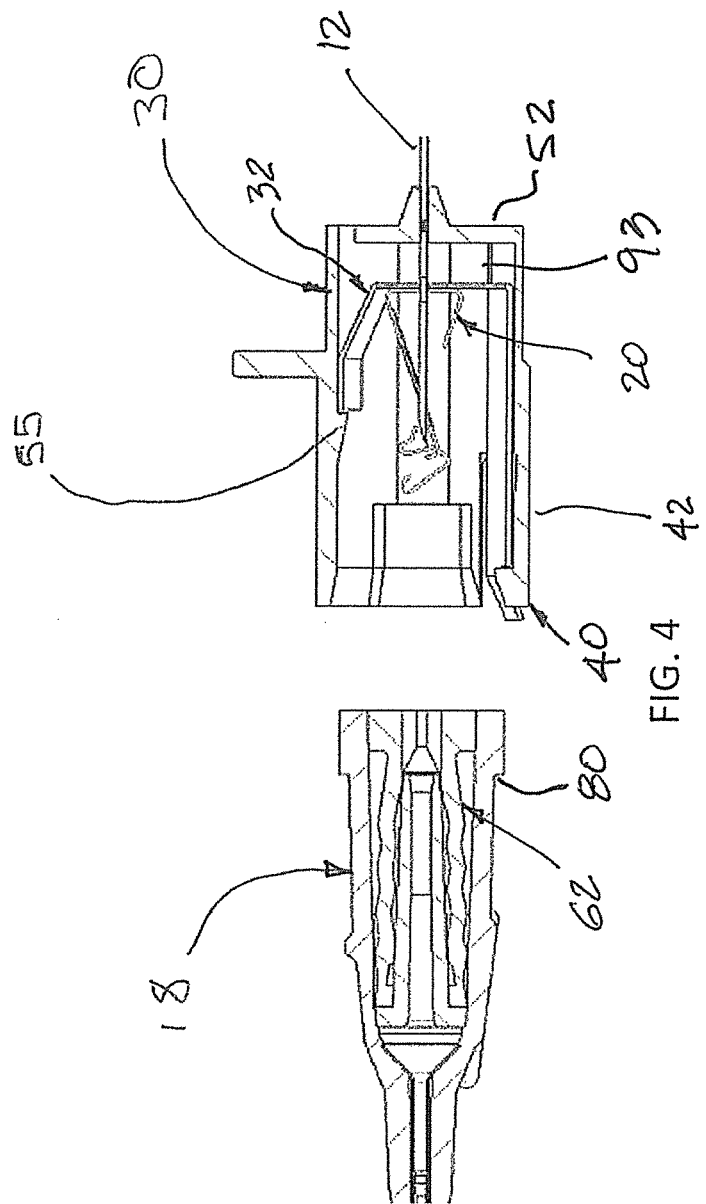
FIG. 4 shows a side cross section view of a separated catheter hub and housing, prior to activating the release element.

With reference to FIG. 2D in addition to FIG. 2C, the arm 42 is unitarily formed with the guard housing 30, such as being molded with the guard housing 30, and has a base 44 unitarily formed with the wall surface 158 of the guard housing 30. Two gaps or spaces are provided on either side of the arm 42 and the shroud 154 to form the arm as a leaf spring having the latch 40 at a distal end of the arm 42. Prior to installation with the guard housing 30 as shown in FIG. 2C, the needle guard 20 is placed in between the short leg 36 and the long leg 38 of the release element 32 and the proximal wall 24 of the needle guard 20 contacts the distally facing side of the proximal wall 34 of the release element 32. The two proximal walls 24, 34 contact one another when assembled as shown and after the release element 32 is placed into the interior receiving space 160 of the guard housing in the ready position. The proximal wall 24 of the needle guard 20 can also be spaced from the proximal wall 34 of the release element 32 in the ready position and move into contact with the release element 32 when moved by the needle 12, such as by the change in profile, during retraction of the needle. In one example, the gap or distance between the short leg 36 and the long leg 38 is larger than the interior distance between the wall surface 158 of the shroud 154 and the arm 42, measured at the arm and the shroud through the center of the shroud. This allows the two legs 36, 38 to bias against the interior of the shroud 154 and the arm 42, as shown in FIG. 4 in the ready position or pre-activation position. In other examples, the gap between the two legs 36, 38 are selected to have a form fit with the interior of the guard housing without extra constraint or biasing.

Figures 3A, 3B, 3C:
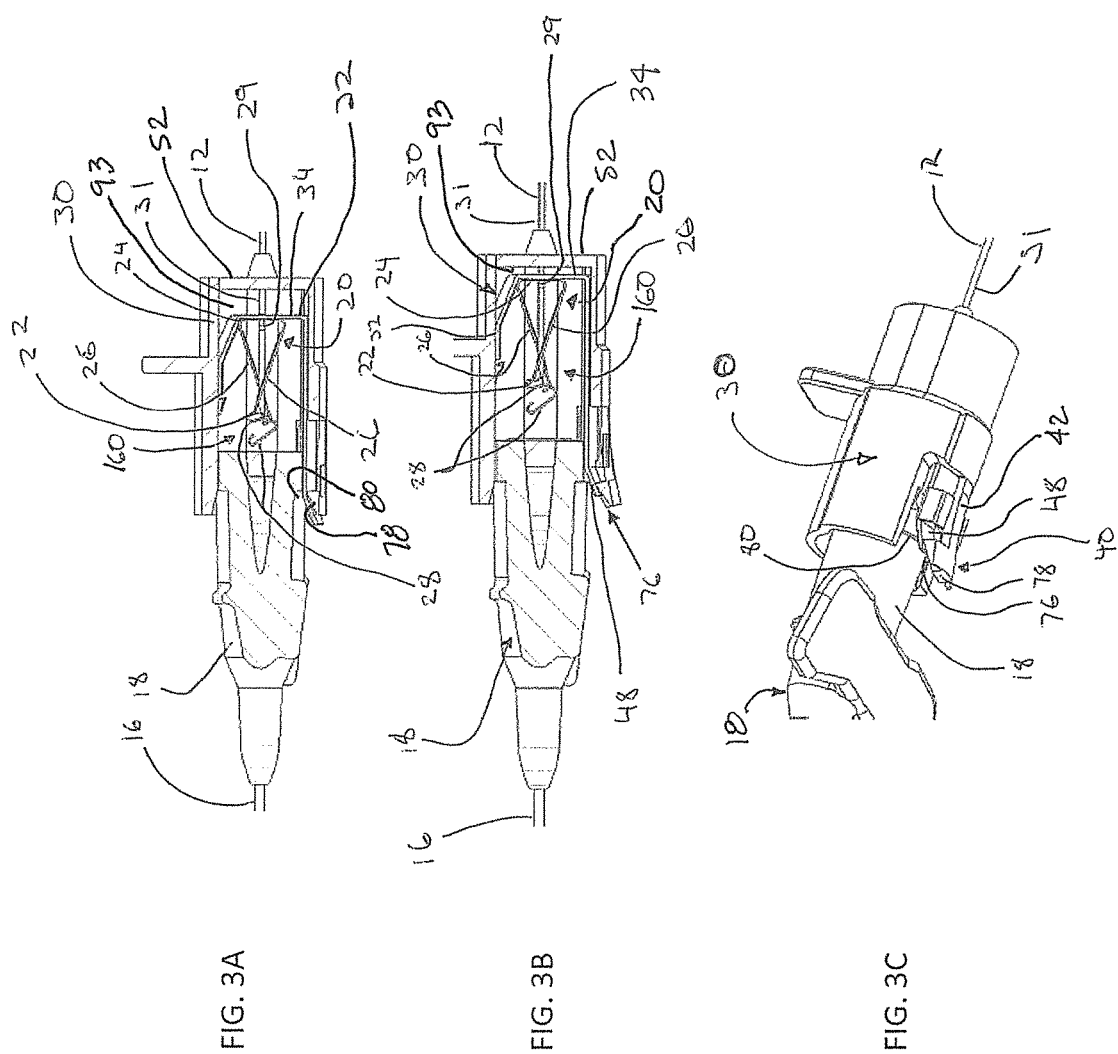
FIG. 3A shows a partial side cross sectional side view of the catheter hub and guard housing with a release element and a needle guard in a pre-activation configuration with the needle tip entering the needle guard but the latch still removably engaged to the catheter hub.
FIG. 3B shows aside cross sectional view of the catheter hub and housing of FIG. 3A with the release element activated to release its engagement with the catheter hub.
FIG. 3C shows a bottom perspective view of the catheter hub and housing of FIG. 3B, with the release element activated.
Figure 5:
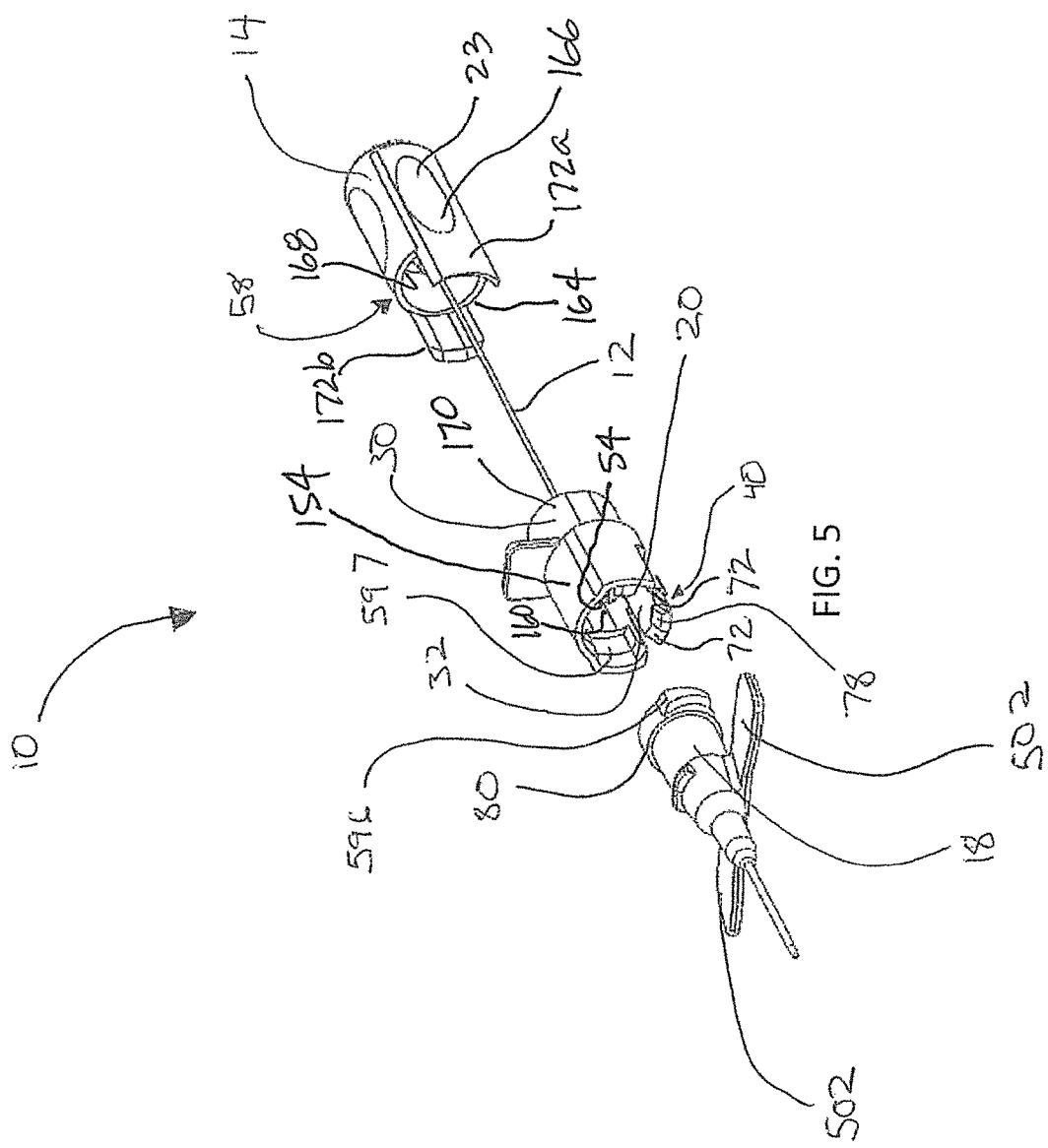
FIG. 5 shows a perspective view of a separated catheter hub, housing and needle hub.

When the needle device 10 is in the ready position with the needle tip projecting out the distal end of the catheter tube 16, which is partially shown in FIG. 2A, the proximal wall 24 of the needle guard 20 can contact the proximal wall 34 of the release element 32. The short leg 36 rests against the interior of the wall surface 158 of the housing 30 and the distal end of the short leg 36 can wedge proximally of a shoulder 55 (FIG. 4) formed in the interior of the guard housing 30. The shoulder 55 can prevent the short leg 36 from moving axially to prevent distal movement of the release element 32 relative to the housing. The latch or terminal end 40 of the arm 42 on the housing 30 slides through the space defined by two retainers 46 and the two ramps 72 of the latch 40 rest between the lifters 48 and the retainers 46. As best seen in FIGS. 2B, 2C, and 5, the two lifters 48, which are sloped, overlay or rest on the sloped surfaces 76 of the two ramps 72 and the projection 78 of the latch 40 is positioned in the space or gap between the two lifters 48. The proximal wall 34 of the release element 32 is located distal of a proximal wall 52 of the housing 30 but proximal of the proximal wall 24 of the needle guard 20 when the needle device is in the ready position. The proximal wall 34 of the release element 32 and the proximal wall 52 of the housing 30 are not in contact in the ready position, such as being spaced from one another, as shown in FIG. 4. This space between the proximal wall 52 of the guard housing 30 and the proximal wall 34 of the release element 32 may be referred to as an actuation gap or space 93 (FIG. 3A). The actuation gap 93, measured between the proximal wall 34 of the release element 32 and the proximal wall 52 of the guard housing 30, has a first dimension or distance when the needle device is in a ready to use position and a second dimension or distance when the needle device is actuated or activated, which is understood to be a configuration where the release element is moved to release the latch 40 from the catheter hub 18. As further discussed below, when this actuation gap 93 changes from a first distance to a second distance, the release element 32 will cause the arm 42 on the guard housing 30 to release from the catheter hub 18, as further discussed below. In an example, the second distance is smaller than the first distance. In some examples, the second distance can be zero to several millimeters, such as about 1-8 mm and possibly more depending on the application.

A recess formed on the exterior surface of the catheter hub 18 defines a ridge 80, as shown in FIGS. 1 and 5. The recess on the body of the catheter hub 18 can be annular or formed in sections just distal of the threads 596. During assembly, the latch 40 on the arm 42 of the guard housing 30 can engage the ridge 80 to removably secure the guard housing 30 to the catheter hub 18. With reference to FIGS. 2A, 2C, and 5, a distal opening 54 of the housing 30 is sized and shaped to receive a proximal end 56 of the catheter hub 18 into the interior receiving space 160 defined by the shroud 154. A projection 78 on the latch 40 at the terminal end of the arm 42 has a lip or shoulder that mechanically engages the ridge 80 on the catheter hub 18. The engagement resembles a detent. In other examples, the projection 78 engages the exterior threads 596 on the catheter hub 18 or a projection formed on the wall surface of the catheter hub. As shown, the ridge 80 allows the guard housing 30, such as the arm 42 of the guard housing, to removably engage with the catheter hub 18 in the ready to use position with the needle tip projecting out a distal end of the catheter tube 16 and during retraction of the needle 12 in the proximal direction following successful venipuncture until the change in profile 29 on the needle 12 engages the proximal wall 24 of the needle guard 20 to move the needle guard and the release element 32 to then cause the arm 42 to move radially outwardly to separate from the catheter hub 18, as further discussed below. In another example, the release element 32, such as the long leg 38 of the release element, engages the catheter hub 18 directly and the arm 42 on the latch 40 on the guard housing is omitted. In other words, the long leg 38 of the release element 32 can be a latch without a separate latch.

During assembly as the proximal end 56 of the catheter hub 18 enters the distal opening 54 of the housing 30, the arm 42 flexes radially outward due to the girth of the catheter hub being larger than the space between the arm 42 and the wall surface 158 of the guard housing 30. For example, the threads on the catheter hub can cause the arm 42 to deflect radially outwardly during the assembly process. With continued insertion of the catheter hub 18 into the receiving space 160 of the guard housing 30 and after the projection 78 on the arm 42 clears the ridge 80 (FIG. 5) on the catheter hub 18, the arm 42 flexes back radially inward, bringing the projection 78 distal and inside the outer diameter of the ridge 80 to removably engage the guard housing 30 to the catheter hub 18. Thus, the projection 78 on the arm 42, which has a lip or ledge, engages the ridge 80 on the catheter hub 18 to removably secure the housing 30 to the catheter hub 18, similar to a detent. This mechanical engagement prevents accidental detachment of the housing 30 from the catheter hub 18 and prevents the catheter hub 18 from moving distally relative to the housing until the engagement is released. In other words, the engagement is a mechanism that guards against premature activation of needle device 10, which can otherwise allow the housing 30 to separate from the catheter hub 18 before the needle tip enters the needle guard 20. To disengage the projection 78 on the latch 40 from the ridge 80 on the catheter hub 18, the release element 32 is moved relative to the latch 40 to cause the lifters 48 on the long leg 38 to move the latch 40 radially outwardly, such as by camming action or camming movement, to separate the detent engagement, as further discussed below.

As shown in FIGS. 2C and 5, sloped operative surfaces 76 on each of the two ramps 72 and on either side of the projection 78 are provided, which sloped upwardly in the proximal direction. The operative surfaces 76 are configured as cam surfaces for releasing the projection 78 on the arm 42 from the notch or ridge 80 on the catheter hub 18. The two lifters 48 on the release element 32 can be provided with the same inclined taper as the two operative surfaces 76 of the latch 40 with different slopes or tapers contemplated.

Figure 2E:
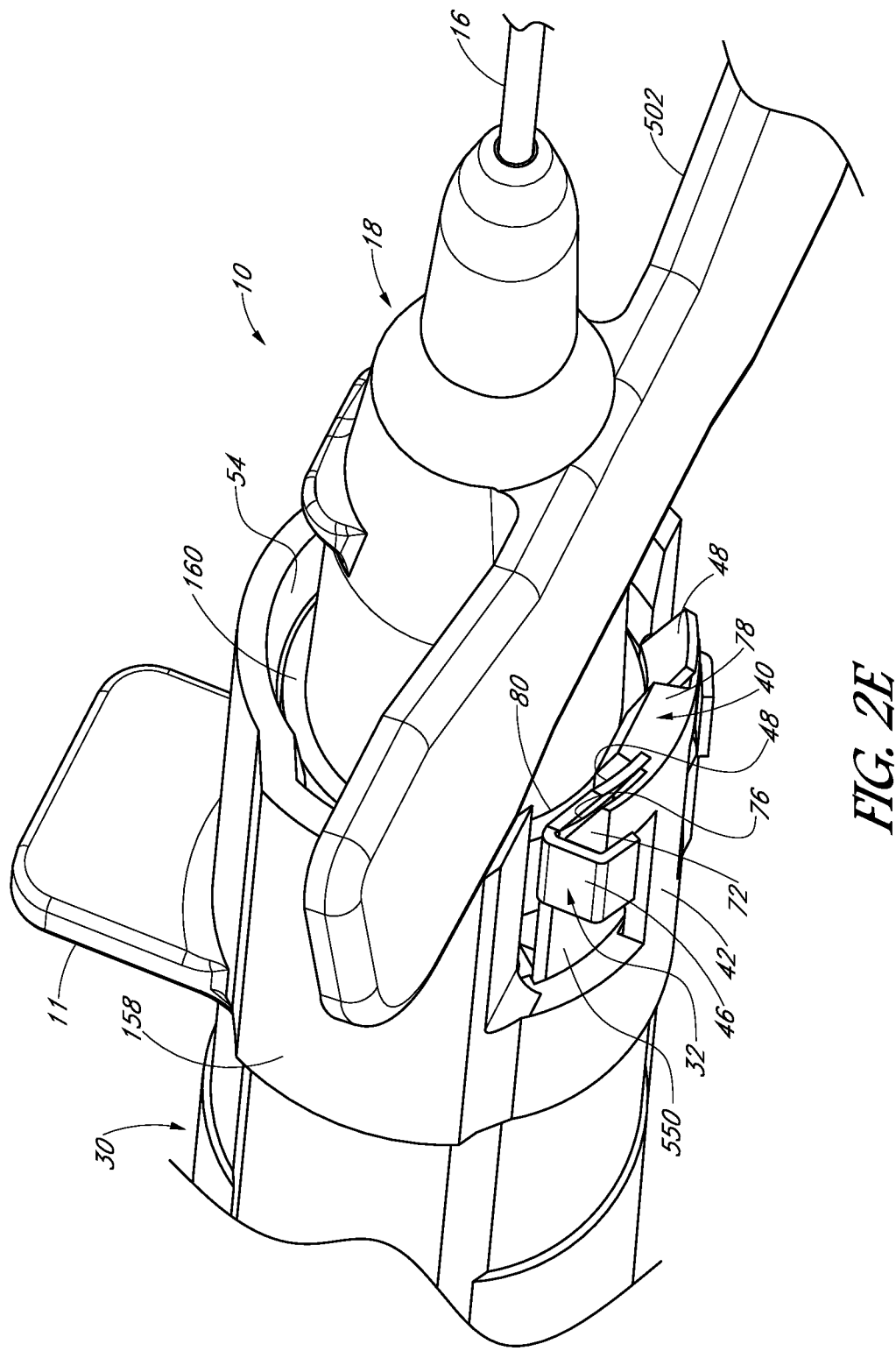
FIG. 2E shows a partial perspective view of the assembly of FIG. 2D along a different viewing angle.

FIG. 2E is a partial detailed view of the needle device 10 of FIG. 1 in the ready to use position. Lines depicting surface features may be omitted unless stated otherwise, such as when depicting a change in contour or a structural feature then the lines can be included. As shown, the projection 78 on the latch 40 engages the ridge 80 of the catheter hub 18 to removably secure the guard housing 30 to the catheter hub 18. Also shown are retainers 46 on the long leg 38 of the release element 32 securing a rib section 550 on each side of the arm 42. The two lifters 48 on the release element 32 overlie the two ramps 72 on the latch 40, and specifically overlie the two sloped operative surfaces 76 of the latch 40.

When the long leg 38 of the release element 32 moves in the proximal direction by the needle guard 20, which is moved by the change in profile 29 on the needle 12 engaging the proximal wall 24 of the needle guard 20 and moving the needle guard in the proximal direction, the lifters 48 are moved in the proximal direction relative to the arm. For example, the lifters can move relative to the operative surfaces 76 of the latch 40. Because the lifters 48 on the release element 32 and the operative surfaces 76 on the latch 40 are both sloped, movement of the lifters 48 relative to the sloped surfaces 76 of the ramps 72 causes the latch 40 to cam and the arm 42 to deflect radially outwardly, which separates the projection 78 from the notch or ridge 80 on the catheter hub 18 to release the housing 30 from the catheter hub 18, as further discussed below with reference to FIGS. 3A-3D.

FIG. 3A shows the needle device 10 in a needle retracted position, such as following successful venipuncture, with the needle tip 22 retracted proximally of the two distal walls 28 of the needle guard 20 and the latch 40, such as the projection 78, still engaging the ridge 80 of the catheter hub 18. The change in profile 29 on the needle 12 is about to contact the proximal wall 24 of the needle guard 20 or contacts the proximal wall of the needle guard but has not moved the proximal wall 24 in the proximal direction to change the actuation gap 93, such as to decrease the actuation gap 93. In the needle retracted position of FIG. 3A, the actuation gap 93 is at a first distance, which is generally the same distance as when the needle device 10 is in a ready to use position. FIG. 3B shows the needle 12 of FIG. 3A further retracted in the proximal direction so that the change in profile 29 on the needle 12 interacts with the proximal wall 24 of the needle guard 20 and moves the proximal wall 24 in the proximal direction relative to the proximal wall 52 of the guard housing 30. As previously discussed, movement of the proximal wall 24 of the needle guard 20 moves the proximal wall 34 of the release element 32 in the proximal direction to decrease the actuation gap 93, which is shown in FIG. 3B with a smaller gap than the actuation gap 93 of FIG. 3A.

As shown in FIGS. 2A and 5, the needle guard 20 is located inside the interior receiving space 160 of the shroud 154 of the guard housing 30 and proximal of the catheter hub 18. The needle hub 14 has a wall surface 166 with a distal opening 164 that opens into a receiving space 168. The guard housing 30 has a proximal elongated extension 170 that is sized and shaped to project into the receiving space 168 of the needle hub 14 in the ready position. The proximal elongated extension 170 can include shaped or contoured surfaces that mate with corresponding interior surfaces of the distal receiving space 168 to angularly align with the needle hub 14. The close fit configuration can also limit relative rotation between the housing 30 and the needle hub 14. In an example, two distally extending wall panels 172a, 172b are provided on the needle hub 14 for overlapping with side surfaces of the housing 30 when in the ready position. The two distally extending wall panels 172a, 172b can be shaped so as to form fit around curved portions of the proximal elongated extension 170 of the guard housing 30. For example, the proximal elongated extension 170 has a generally straight or flat section on each side of the housing 30 corresponding to the locations of the two distally extending wall panels 172a, 172b of the needle hub 14. The two distally extending wall panels 172a, 172b can also incorporate corresponding straight or flat sections to closely receive the proximal elongated extension 170 when assembled. Because the two distally extending wall panels 172a, 172b are spaced from one another, the proximal elongated extension 170 is exposed or not covered at the gaps between the two panels 172a, 172b, when in the ready to use position. The needle 12 extends in a distal direction from the needle hub 14 through openings in the proximal walls of the housing 30, the release element 32, and the needle guard 20 and through the catheter hub 18 and the catheter tube 16 in the ready to use position.

Referring again to FIG. 2A, in the ready position, the two arms 26 of the needle guard 20 are biased outwardly by the needle shaft 31. In some examples, the shroud 154 of the guard housing 30 is provided with one or more ledges so that the ends of the needle guard, such as the ends of the distal walls 28, rest on the one or more ledges and be spaced from the needle in the ready position and during retraction of the needle following successful venipuncture. Although the flashback chamber of the needle hub 14 is shown reduced, a more traditional or standard flashback chamber may be incorporated with a vent plug.

FIGS. 3A-3C shows the device 10 of FIG. 1A in a sequence of steps during retraction of the needle 12 away from the catheter hub 18, similar to steps following placement of the of the catheter tube 16 into a patient's vein. Refer initially to FIG. 3A, the needle 12 is shown withdrawn from the catheter tube 16 and the catheter hub 18 and the needle tip 22 moves proximally of the two distal walls 28 on the two arms 26 of the needle guard 20. As the two arms 26 on the needle guard 20 are resilient and no longer held by the presence of the needle shaft 31, the arms 26 move radially and the distal walls 28 cover the needle tip 22, which is shown in FIG. 3A. The guard housing 30 remains engaged to the catheter hub 18 due to the engagement between the latch 40 of the guard housing 30, for example the projection 80 on the latch 40, and the ridge 80 on the catheter hub 18, as previously described. At this point, the change in profile 29 on the needle 12 is about to or just touches the proximal wall 24 of the needle guard 20 but has not moved the proximal wall 24 of the needle guard in the proximal direction. The actuation gap 93 is at a first distance or dimension at this point, which is the same or approximately the same as during insertion of the needle device into a patient's vein.

As the needle 12 continues to move in the proximal direction, the change in profile 29 on the needle shaft 31 makes contact with the proximal wall 24 of the needle guard 20, such as contacting the perimeter defining the proximal opening on the proximal wall. As shown in FIG. 3B, due to the contact between the change in profile 29 and the proximal wall 24 of the needle guard, further proximal movement of the needle 12 moves the proximal wall 24 and hence the needle guard 20 proximally. If a space is provided, the proximal wall 24 moves to abut the proximal wall 34 of the release element 32. Due to the contact between the proximal wall 24 of the needle guard 20 and the proximal wall 34 of the release element 32, the release element 32 also moves proximally with the needle guard 20 as the needle moves in the proximal direction after the engagement between the change in profile 29 and the needle guard 20. As the release element 32 moves proximally or rearward, the contacts between the lifters 48 and the sloped operative surfaces 76 of the ramps 72 on the latch 40 of the guard housing 30 cause the ramps 72 to move or deflect due to the cam action between the lifters 48 and the sloped operative surfaces 76. This in turn moves the latch 40 radially outward due to the camming action. As the latch 40 moves radially outward, the mechanical engagement between the projection 78 and the ridge 80 on the catheter hub 18 is released to disengage the housing 30 from the catheter hub 18. Once the projection 78 clears the outer diameter of the ridge 80, continued proximal movement of the needle hub 14 in the proximal direction will pull the housing 30 proximally along with the needle guard 20 and the release element 32, separating the housing 30 from the catheter hub 18, as shown in FIG. 5. The actuation gap 93 once the release element 32 is actuated is now at a second dimension, which is smaller than the first dimension shown in FIG. 3A. The latch 40 being deflected radially outwardly by the camming action of the lifters 48 on the release element 32 is more clearly shown in FIG. 3C, which shows the projection 78 on the latch 40 separated from the ridge 80 on the catheter hub 18.

FIG. 3D is a front perspective view of FIG. 3C. Lines depicting surface features may be omitted unless stated otherwise, such as when depicting a change in contour or a structural feature then the lines can be included. As shown, the projection 78 on the latch 40 is spaced or separated from the ridge 80 on the catheter hub 18. The latch 40 is radially deflected outwardly to separate the projection 78 on the latch 40 from the ridge 80 by the camming action between the lifters 48 and the sloped operative surfaces 76 of the two ramps 72, on either side of the projection 78. No longer engaged to one another, the guard housing 30, along with the needle guard 20 and the release element 32 located inside the guard housing 30, can now separate from the catheter hub.

Figure 4A:
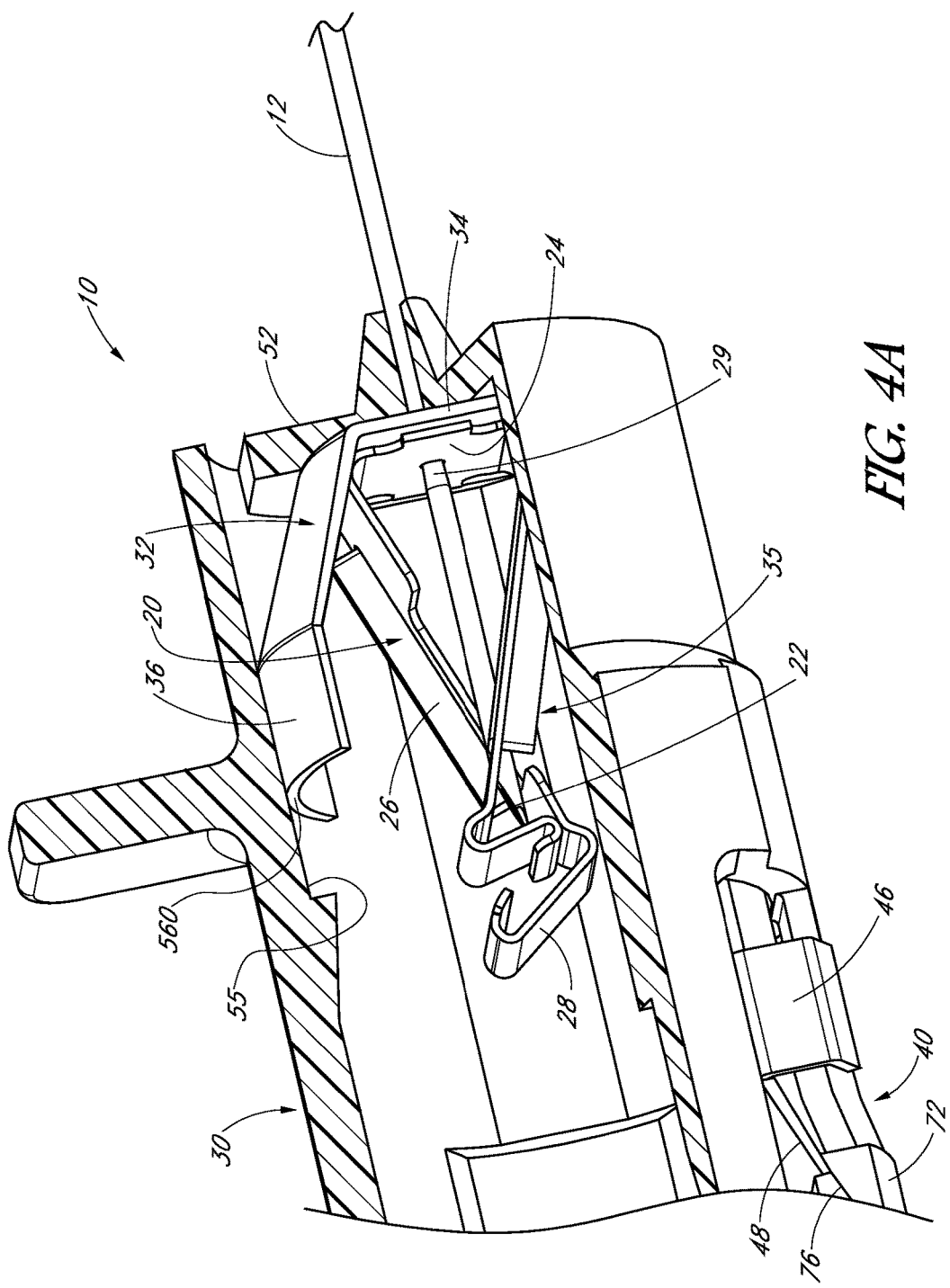
FIG. 4A shows a partial cross sectional perspective view of the housing and release element with the release element retracted, similar to FIG. 3B.

FIG. 4A is a partial cut-away view of the needle device 10 of FIG. 3D in the activated position. Lines depicting surface features may be omitted unless stated otherwise, such as when depicting a change in contour or a structural feature then the lines can be included. As shown, the needle guard 20 and the release element 32 have moved in the proximal direction due to the engagement of the change in profile 29 on the needle 12 and the proximal wall 24 of the needle guard 20 during retraction of the needle 12 from the catheter tube and catheter hub. The proximal movement causes the two lifters 48 (only one shown) to push on the sloped operative surfaces 76 of the ramps (only one shown) on the latch 40, which causes the projection 78 to separate from the ridge 80 on the catheter hub 18 (FIG. 3D). Also clearly shown is the separation between the distal edge 560 of the short leg 36 away from the shoulder 55 in the interior cavity of the guard housing 30. In an example, this gap is equal to the distance the proximal wall 34 of the release element 32 moves towards the proximal wall 52 of the guard housing 30.

Thus, an aspect of the present disclosure is understood to include a needle device comprising a catheter hub with a catheter tube, a flow control regulator or flow regulator positioned inside the interior cavity of the catheter hub, a needle guard positioned inside a shroud of a guard housing, which is removably engaged to the catheter hub, and a needle hub having a needle projecting through the guard housing, the needle guard, the catheter hub, and the catheter tube and having a tip extending distally out a distal opening of the catheter tube. The needle hub can optionally include a distal receiving space for receiving a proximal elongated section of the guard housing. The needle hub can optionally include distally extending wall panels that straddle two sides of the guard housing. The flow control regulator can comprise a compressible elastic sleeve. The flow control regulator can comprise an elongated stem with a flow channel located inside the compressible elastic sleeve. A release element may be positioned inside the housing and has a proximal wall that is located between a proximal wall of the needle guard and a proximal wall on the guard housing. The proximal wall of the release element can be spaced from the proximal wall of the guard housing by an actuation gap having a first distance when in a ready position. The proximal wall of the release element can be spaced from the proximal wall of the guard housing by an actuation gap having a second distance when the needle device is actuated, which is smaller than the first distance. The release element can include lifters for interacting with a latch on an arm on the guard housing. The guard housing can engage the catheter hub by way of a projection on the latch of the arm engaging a shoulder, ridge or notch on the catheter hub. The projection can separate from the ridge or notch on the catheter hub by causing the lifters on the release element to push the latch on the arm of the housing radially outwardly away from a lengthwise axis of the device. The pushing action by the lifters can resemble a caroming action between tapered surfaces on the lifters and tapered surfaces on the ramps of the latch on the arm. The needle can comprise a change in profile. The change in profile can engage a perimeter defining an opening on the needle guard when the needle moves in a proximal direction following successful venipuncture. Upon retraction of the needle guard by the needle, the needle guard can push on the release element, which can cause the lifters to move the arm to separate from the catheter hub and the actuation gap to move from a first distance to a second distance, which is smaller than the first distance. Further retraction of the needle can separate the housing from the catheter hub.

FIG. 5 shows the needle device 10 with the catheter hub 18 separated from the housing 30 and the needle hub 14. In some embodiments the catheter hub 18 has stabilization elements 502, which may comprise a pair of laterally extending wings. In other embodiments, the stabilization elements are omitted. The wings may be secured to the patient to secure the puncture site from moving, such as with medical tape. As shown, the catheter hub 18 includes threads 596 on the proximal end thereof, which provides the catheter hub 18 with a female threaded Luer. In some examples, the notch or ridge 80 for engagement by the projection 78 on the arm latch 40 is shown as an annular recess. In other examples, only the area or section of the catheter hub 18 where the projection 78 on the latch 40 engages the catheter hub has a recess. In still other examples, the projection 78 can engage the threads 596 on the catheter hub without a separate recess forming the ridge 80. The threads 596 align with corresponding slots or channels 597 formed in the interior of the housing guard 30 to facilitate receiving the proximal end of the catheter hub into the interior space 160 of the housing. The slots or channels 597 extend from the distal opening of the housing 30 to a point sufficiently proximal to allow the projection 78 on the latch 40 of the arm 40 to engage the ridge 80 on the catheter hub 18 to removably secure the housing 30 to the catheter hub 18. With the threads 596 located in the slots or channels 597 of the guard housing 30, the catheter hub 18 is restricted from freely rotating relative to the housing 30 in the ready to use position. This ensures that the stabilization elements 502, when they are present, are properly positioned relative to a patient during venipuncture.

With reference now to FIG. 6, a schematic cross-sectional view of an alternative needle device 300 is shown, which may also be referred to as a catheter assembly. The needle device 300 is shown with a catheter hub 302, a catheter tube 304 extending distally of catheter hub 302 and held thereto by a bushing 306, and a flow regulator 308 located inside the interior cavity 334. The present needle device 300 is understood to include a guard housing 30 with a release element 32, a needle guard 20, a needle 12, and a needle hub 14, similar to that shown in FIG. 1A. The needle device 300 of the present embodiment operates very similarly to the device 10 of FIG. 1A with a few exceptions, as discussed below. Primarily, the present flow regulator 308 uses a different stem and compressible sleeve combination than the stem and compressible sleeve combination of FIGS. 1B and 1C.

As shown, an elongated stem 310 comprising a proximally extending conical projection 312 having a central flow path 314 is provided inside the bore 316 of the catheter hub. The conical projection 312 has a proximal opening having a dimension that is smaller than the width at the base of the conical projection, which is distal of the opening. The conical projection 312 is attached to a flange or a plate 318, which serves to hold the stem 310 inside the bore of the catheter hub 302. In one example, the elongated stem 310 is separately formed, such as by a plastic or metal material, and subsequently attached to the bore 316, such as be wedging, snap fit, or interference fit. The flange or plate 318 is fixed to the interior of the catheter hub 302 so that a valve 320 may be pushed there-against to open the valve and permit fluid communication between a male medical implement and the interior of the catheter hub, such as the distal chamber 321 of the catheter hub and the catheter tube 304 and a syringe. The valve 320 is compressible and, relative to the elongated stem 310, may be referred to as a compressible sleeve 320 located around the elongated stem 310.

As shown, the valve 320 comprises a push end 322, a septum 324 having one or more slits, and a resilient section 326. The push end 322 is sized and shaped to be abutted by a nose section of a male medical implement to advance the valve 320 into the stem 310 to open the one or more slits in the septum 324 to then permit fluid flow across the valve. In an example, the push end 322 comprises a component that can take an axial force to advance against the actuator. For example, the push end can comprise a ring with a ring end 330 being sized and shaped to be abutted by the nose section of a male medical implement. In other examples, the push end 322 is non-continuous, such as having channels or notches and not a complete ring. The push end can be made from a hard and/or a rigid material, such as hard plastic, engineered plastic, or a metal.

The septum 324 is made from an elastic material, such as silicone, and is coupled to the push end 322. For example, the septum may embody a disc shape with an outer circumference of the disc contoured to mate with seats, channels, or grooves on the push end 322 to couple to the push end. In other examples, the septum 324 is glued to the push end 322 instead of or in addition to mechanical engagement. At a central area of the disc, the septum is provided with one or more slits to form two or more flaps. The flaps can deflect and open to permit fluid communication by pushing the valve 320 against the stem 310 and the tip end of the actuator projecting into the septum to deflect the one or more flaps.

The resilient section 326 is attached to the septum 324 and the push end 322, either directly or indirectly. In the example shown, the resilient section 326 serves as a biasing element to return the valve 320 to its un-opened position shown in FIG. 6 after the male medical implement is removed from the proximal opening of the catheter hub. In one example, the resilient section 320 has a surface that pushes against the actuator to return the valve to the un-opened position. The resilient section 326 can have a resilient surface that presses against the actuator to return the valve to the un-opened position. The resilient section 326 can alternatively have legs or a proximal end surface that pushes against a surface of the catheter hub or against the surface of the flange or plate 318 of the actuator to return the valve to the un-opened position.

FIG. 7 shows the device 300 of FIG. 6 in a used position, such as following successful venipuncture and following removable of the needle, needle guard, and housing that retains the needle guard in the ready to use position. The valve 320 is shown advanced against the conical projection 312, such as by a male Luer tip, and the proximal tip of the stem 310 is pushed into the septum 324 to open one or more flaps. Fluids can now be introduced across the valve and through the catheter hub and catheter tube. Samples can also be taken from the catheter hub when the valve 320 is in the opened position as shown.

Method for manufacturing or making and using the needle devices and their components discussed elsewhere herein are within the scope of the present disclosure.

Although limited embodiments of the needle devices and their components have been specifically described and illustrated herein, many modifications and variations will be apparent to those skilled in the art. Furthermore, it is understood and contemplated that features specifically discussed for one needle device embodiment may be adopted for inclusion with another needle device embodiment, provided the functions are compatible. For example, release element may be integrated with the needle guard. Accordingly, it is to be understood that the needle devices and their components constructed according to principles of the disclosed device, system, and method may be embodied other than as specifically described herein. The disclosure is also defined in the following claims.

What is claimed is:

1. A needle device comprising:
   a needle hub with a needle with a needle tip extending in a distal direction;
   a catheter hub distal of the needle hub and comprising an interior cavity and a catheter tube extending distally of a distal end of the catheter hub;
   a guard housing located at least in part between the catheter hub and the needle hub and having a movable arm and a wall surface defining a cavity;
   a release element located at least partially inside the cavity of the guard housing and having a surface in mechanical communication with the movable arm;
   wherein the needle projects through the guard housing, the catheter hub, and the catheter tube and out a distal end of the catheter tube in a ready to use position; and
   wherein part of the movable arm on the guard housing engages an exterior of the catheter hub and the movable arm is deflectable by action of the release element, and the release element is movable by action of the needle to release the engagement between the part of the movable arm and the exterior of the catheter hub.

2. The device of claim 1, wherein the arm is movable by a camming motion.

3. The device of claim 1, further comprising a needle guard comprising a proximal wall having a perimeter defining a proximal opening located in the guard housing.

4. The device of claim 3, wherein the needle guard comprises two arms that intersect one another along a side view in both the ready to use position and in a protective position.

5. The device of claim 1, further comprising a flow regulator located in the interior cavity of the catheter hub.

6. The device of claim 5, wherein the flow regulator comprises an elongated stem and a compressible sleeve surrounding the elongated stem.

7. The device of claim 6, wherein the elongated stem comprises a base fitted against an interior surface of the catheter hub.

8. The device of claim 6, wherein the elongated stem has a blunt end and a flow path.

9. The device of claim 6, wherein the elongated stem comprises a conical projection having a flow path.

10. The device of claim 9, wherein the elongated stem is attached to a flange.

11. The device of claim 6, wherein the compressible sleeve comprises a septum.

12. The device of claim 6, wherein the compressible sleeve has a proximal end surface that is flushed with a proximal end of the catheter hub.

13. The device of claim 6, wherein the elongated stem is configured to push through a septum on the compressible sleeve.

14. The device of claim 6, wherein the compressible sleeve comprises a plurality of folds when compressed by a male medical implement.

15. The device of claim 1, wherein the arm comprises a latch with a projection that engages the catheter hub.

16. The device of claim 15, wherein the projection engages exterior threads formed on an exterior of the catheter hub.

17. The device of claim 1, wherein the release element comprises at least one lifter.

18. The device of claim 1, wherein the release element has a proximal wall with a perimeter defining an opening, a short leg, and a long leg, which is longer in length than the short leg.

19. The device of claim 18, wherein the long leg comprises two lifters and wherein the two lifters are tapered relative to a lengthwise axis of the needle.

20. The device of claim 18, wherein the arm is located externally of the long leg.

21. The device of claim 20, wherein retainers extend from the long leg and wrap, at least in part, around the arm.

22. The device of claim 1, wherein the guard housing has a proximal elongated extension projecting into the needle hub.

23. The device of claim 22, wherein the needle hub has two spaced apart wall panels for receiving the proximal elongated extension.

24. The device of claim 1, further comprising a plug attached to a proximal end of the needle hub.

25. A method of manufacturing a needle device comprising:
   forming a needle hub with a needle with a needle tip extending in a distal direction;
   forming a catheter hub comprising an interior cavity and a catheter tube extending distally of a distal end of the catheter hub and placing the catheter hub distal of the needle hub;

forming a guard housing with a movable arm and a wall surface defining a cavity, and placing the guard housing at least in part between the catheter hub and the needle hub;

placing a release element at least partially inside the cavity of the guard housing and a surface of the release element in mechanical communication with the movable arm;

wherein the needle projects through the guard housing, the catheter hub, and the catheter tube and out a distal end of the catheter tube in a ready to use position; and wherein part of the movable arm on the guard housing engages an exterior of the catheter hub and the movable arm is deflectable by action of the release element, and the release element is movable by action of the needle to release the engagement between the part of the movable arm and the exterior of the catheter hub.

* * * * *